United States Patent [19]
Garson et al.

[11] Patent Number: 6,136,528
[45] Date of Patent: *Oct. 24, 2000

[54] MULTIPLE SCLEROSIS VIRUS

[75] Inventors: Jeremy Garson; Philip Tuke, both of London, United Kingdom

[73] Assignees: University College London, London, United Kingdom; Biomerieux S.A., Marcy l'etoile, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/553,411

[22] PCT Filed: May 24, 1994

[86] PCT No.: PCT/GB94/01129

§ 371 Date: Mar. 18, 1996

§ 102(e) Date: Mar. 18, 1996

[87] PCT Pub. No.: WO94/28138

PCT Pub. Date: Dec. 8, 1994

[30] Foreign Application Priority Data

May 24, 1993 [GB] United Kingdom .................. 9310657

[51] Int. Cl.[7] .............................. C12Q 1/70; C12Q 1/68; C12N 15/09; C12N 15/63
[52] U.S. Cl. .................................. 435/5; 435/6; 435/7.1; 435/320.1; 536/23.1; 536/23.72; 536/24.3; 530/326; 530/327
[58] Field of Search ................................ 435/5, 6, 320.1, 435/240.1, 7.1; 536/23.1, 23.72, 24.3; 530/326, 327

[56] References Cited

FOREIGN PATENT DOCUMENTS

| 0 222 310 | 5/1987 | European Pat. Off. ...... G01N 33/569 |
| 92/08785 | 5/1992 | WIPO .............................. C12N 7/00 |

OTHER PUBLICATIONS

Poiesz, et al. : Polymerase chain reaction and the detection . . . : J. Ceel. Biochem. :Suppl. 13E: abstracts WH 224, Apr. 1989.

Maniatis, et al. : Molecular Cloning a laboratory manual: Cold Spring Harbor: pp. 431–433, 1982.

*Primary Examiner*—Jeffrey Stucker
*Assistant Examiner*—Brett Nelson
*Attorney, Agent, or Firm*—Browdy and Neimark

[57] ABSTRACT

The present invention provides a polynucleotide in substantially isolated form comprising a sequence of nucleotides which is capable of selectively hybridizing to the genome of the human multiple sclerosis virus (HMSV) or the complement thereof, wherein HMSV is characterized by:

(i) a positive stranded RNA genome;
(ii) said genome comprising one or more open reading frames (ORF) encoding protein(s) or polyprotein(s);
(iii) said genome encoding a reverse transcriptase enzyme; and
(v) said genome comprising nucleotide sequences which are homologous to or selectively hybridizable with any one of the nucleotide sequences illustrated in SEQ ID NOS:1 to 6.

20 Claims, No Drawings

SEQUENCE LISTING

```
(1) GENERAL INFORMATION:

(iii) NUMBER OF SEQUENCES: 6

(2) INFORMATION FOR SEQ ID NO:1:

(i) SEQUENCE CHARACTERISTICS:
          (A) LENGTH: 80 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

GTCCAACAAT TTGCCAGACG TATGTGGGGC AAGCAATTGA ACCTAGACGT AAAAAATTTT      60

CACAGTGTTA CATTGATCAC                                                  80

(2) INFORMATION FOR SEQ ID NO:2:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (ii) MOLECULE TYPE: cDNA
```

-continued

```
    (xi) SEQUENCE DESCRIPTION: SEQ ID NO:2:

AGAGATAGCC TCCACCTCTT TGGACAGGCT CTAGCTAGGG ACTTGTGCAC CCTGCAG         57

(2) INFORMATION FOR SEQ ID NO:3:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TAGGACAAAA TATGTCATGC AAGTTCTTTT CCATAAGTCA CGCTCTGTAC TTACTTATTC       60

TGCATATACT ACTGTCCCTT CACATT                                           86

(2) INFORMATION FOR SEQ ID NO:4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGCTGAAGCC TATCGCGTGC AGTTGCCGGA TGCCGCCTAT AGCCTC                     46

(2) INFORMATION FOR SEQ ID NO:5:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGCCCAGGCA TCAGCCCCAA GACTTGAGCC AGTCCTCATA CCTGGACACT CTTGTCTTCA       60

G                                                                      61

(2) INFORMATION FOR SEQ ID NO:6:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GTGCTGCAAG GTGCGCTGAA AAATGCCATG GCTTCAGCCA CTTTTAATGA CTTTCCGGCT       60

CCTCGATA                                                               68
```

MULTIPLE SCLEROSIS VIRUS

This application is a 371 of P.C.T. application Ser. No. PCT/GB94/01129, filed May 24, 1994.

The present invention relates to multiple sclerosis and in particular to a virus associated with this disease.

Multiple sclerosis (MS) is a debilitating wasting disease which generally strikes its victims at some time after adolescence. The disease is associated with degeneration of the myelin sheaths surrounding nerve cells which leads to a loss of motor and sensory function.

There are no cures for MS and even attempts to ameliorate the symptoms and slow the progress of the disease have up to now met with only limited success.

Many different theories over the years have been expounded to explain the cause of MS, such as environmental and/or genetic factors. A viral origin has also been postulated although no conclusive data which would support this theory over any others have been demonstrated.

We have now demonstrated that MS is associated with a retrovirus. We have used material from patients with MS, made cDNA and amplified this material by PCR with degenerate oligonucleotide primers based upon a highly condensed region of retroviral polymerase (pol) genes. By this means we have obtained retroviral sequences from a previously unknown retrovirus which we have called human multiple sclerosis virus (HMSV). Our isolate of HMSV is described below as HMSV-1.

The present invention relates to nucleic acids such as DNA or RNA encoding all or part of HMSV genome. The invention also provides polypeptides and fragments thereof of HMSV. The invention further provides antibodies (including polyclonal, monoclonal, single domain and humanised antibodies) and fragments thereof (especially fragments containing an antigen binding site such as Fab' or F(ab)$_2$ fragments) against such peptides.

The peptides, antibodies and fragments thereof of the invention may be incorporated into kits for immunodiagnosis of HMSV.

Portions of the nucleic acid sequences derived from HMSV are useful as probes to diagnose the presence of virus in samples, and to isolate naturally occurring variants of the virus. These sequences also make available polypeptide sequences of HMSV antigens encoded within the HMSV genome(s) and permits the production of polypeptides which are useful as standards or reagents in diagnostic tests and/or as components of vaccines. Antibodies, both polyclonal and monoclonal, directed against HMSV epitopes contained within these polypeptide sequences are also useful for diagnostic tests, as therapeutic agents, for screening of antiviral agents, and for the isolation of the HMSV agent from which these sequences derive. In addition, by utilizing probes derived from these sequence, it is possible to isolate and sequence other portions of the HMSV genome, thus giving rise to additional probes and polypeptides which are useful in the diagnosis and/or treatment, both prophylactic and therapeutic, of MS.

Thus the invention provides a polynucleotide in substantially isolated form comprising a sequence of nucleotides which is capable of selectively hybridizing to the genome of the human multiple sclerosis virus (HMSV) or the complement thereof, wherein HMSV is characterized by:

(i) a positive stranded RNA genome;
(ii) said genome comprising one or more open reading frames (ORF) encoding protein(s) or polyprotein(s);
(iii) said genome encoding a reverse transcriptase enzyme; and
(iv) said genome comprising nucleotide sequences which are homologous to or selectively hybridizable with any one of the nucleotide sequences illustrated in SEQ ID NOS: 1 to 6.

Nucleotide sequences homologous to the sequences of any one of SEQ ID NOS: 1 to 6 will be those in which there is at least 60%, for example 70, 75, 80, 85, 90, or 95% homology over the length of the sequence exemplified. Those of skill in the art will of course appreciate that because the figures illustrate cDNA sequences and the virus is an RNA virus, the bases represented by the letters T and U of the genetic code must be considered equivalent for the purposes of homology measurement.

Similarly, a sequence which is selectively hybridizable to any one of the sequences of SEQ ID NOS: 1–6 will have a degree of homology to the complementary strand of the sequence to which they can hybridize similar to the homology mentioned above.

Accordingly, the features (i) to (iv) provide a "fingerprint" which can be read by those of skill in the art to identify whether or not a retrovirus is HMSV.

Although the presence of a region of sequence from any one of the SEQ ID NOS: 1, 2, 3, 4, 5 or 6 will be indicative of a positive "fingerprint", it may be desirable to confirm that any particular virus is a strain of HMSV by confirmatory epidemiological studies.

Accordingly further aspects to which the invention relates are: a purified HMSV polynucleotide; a recombinant or synthetic HMSV polynucleotide; a recombinant polynucleotide comprising a sequence derived from an HMSV genome or from HMSV cDNA; a recombinant polynucleotide encoding an epitope of HMSV; a recombinant cloning or expression vector containing any of the above recombinant polynucleotides, and a host cell transformed with any of these vectors.

The invention also provides a DNA polynucleotide encoding a polypeptide, which polypeptide comprises a contiguous sequence of at least 10 amino acids encoded by the genome of HMSV, said at least 10 amino acids comprising an antigenic determinant of HMSV, wherein HMSV is characterized by:

(i) a positive stranded RNA genome;
(ii) said genome comprising an open reading frame (ORF) encoding a protein or polyprotein;
(iii) said genome encoding a reverse transcriptase enzyme; and
(iv) said genome comprising nucleotide sequences which are homologous to or selectively hybridizable with any one of the nucleotide sequences of HMSV-1 illustrated in SEQ ID NOS: 1 to 6.

Preferably, the polypeptide encodes 15, 20 or 25 or more amino acids.

Other aspects to which the invention relates are: a recombinant expression system comprising an open reading frame (ORF) of DNA having a sequence derived from an HMSV genome or from HMSV cDNA, wherein the ORF is operably linked to a control sequence compatible with a desired host cell, a cell transformed with the recombinant expression system, and a polypeptide produced by the transformed cell.

The invention can be utilized to obtain purified HMSV particles, a preparation of polypeptides from the purified HMSV; a purified HMSV polypeptide; a purified polypeptide comprising an epitope which is immunologically identifiable with an epitope contained in HMSV.

Thus, the invention provides a polypeptide in substantially isolated form comprising a contiguous sequence of at least 10 amino acids encoded by the genome of human multiple sclerosis virus (HMSV) said contiguous sequence comprising an antigenic determinant of HMSV, wherein HMSV is characterized by:

(i) a positive stranded RNA genome;
(ii) said genome comprising an open reading frame (ORF) encoding a protein or polyprotein;
(iii) said genome encoding a reverse transcriptase enzyme; and
(iv) said genome comprising nucleotide sequences which are homologous to or selectively hybridizable with any one of the nucleotide sequences of HMSV-1 illustrated in SEQ ID NOS: 1 to 6.

Included aspects of the invention are a recombinant HMSV polypeptide; a recombinant polypeptide comprising a sequence derived from an HMSV genome or from HMSV cDNA; a recombinant polypeptide comprising an HMSV epitope; and a fusion polypeptide comprising an HMSV polypeptide. The polypeptide may be attached to a detectable label.

Also included in the invention are an anti-HMSV antibody composition comprising antibodies that bind said antigenic determinant of a polypeptide according to the invention which is (a) a purified preparation of polyclonal antibodies, or (b) a monoclonal antibody composition.

Another aspect of the invention is a virus-like particle which is immunogenic against HMSV infection comprising a non-HMSV polypeptide having an amino acid sequence capable of forming a particle when said sequence is produced in a eukaryotic host, and an HMSV epitope.

Still another aspect of the invention is a polynucleotide probe for HMSV, the probe comprising a polynucleotide of the invention optionally attached to a detectable label.

Aspects of the invention which pertain to kits are those for: analyzing samples for the presence of polynucleotides derived from HMSV comprising a polynucleotide probe containing a nucleotide sequence from HMSV of about 8 or more nucleotides, in a suitable container; analyzing samples for the presence of an HMSV antigen comprising an antibody directed against the HMSV antigen to be detected, in a suitable container; analyzing samples for the presence of antibodies directed against an HMSV antigen comprising a polypeptide containing an HMSV epitope present in the HMSV antigen, in a suitable container.

Other aspects to which the invention relates are: a polypeptide comprising an HMSV epitope, attached to a solid substrate; and an antibody to an HMSV epitope, attached to a solid substrate.

Still other aspects to which the invention relates are: a method for producing a polypeptide containing an HMSV epitope comprising incubating host cells transformed with an expression vector containing a sequence encoding a polypeptide containing an HMSV epitope under conditions which allow expression of said polypeptide; and a polypeptide containing an HMSV epitope produced by this method.

The invention also relates to a method for detecting HMSV nucleic acids in a sample comprising reacting nucleic acids of the sample with a probe for an HMSV polynucleotide under conditions which allow the formation of a polynucleotide duplex between the probe and the HMSV nucleic acid from the sample; and detecting a polynucleotide duplex which contains the probe. The method may comprise the use of a polymerate chain reaction (PCR).

Immunological tests and immunoassays are also included in the invention. These include an immunoassay for detecting an HMSV antigen comprising (a) providing an antibody composition according to the invention; (b) incubating a sample with the antibody composition under conditions that allow for the formation of an antibody-antigen complex; and (c) detecting antibody-antigen complexes comprising the anti-HMSV antibodies. The invention also provides an immunoassay for detecting antibodies directed against an HMSV antigen comprising (a) incubating a polypeptide comprising an antigenic determinant bindable by said anti-HMSV antibody, wherein said antigenic determinant is encoded by the genome of HMSV; (b) incubating a biological sample with said polypeptide under conditions that allow for the formation of an antibody-antigen complex; and (c) detecting antibody-antigen complexes comprising said polypeptide.

The invention also provides vaccine compositions for treatment of HMSV infection comprising an immunogenic peptide containing an HMSV epitope, or an inactivated preparation of HMSV, or an attenuated preparation of HMSV.

An application of the invention is a tissue culture grown cell infected with HMSV. Methods for culturing primary or immortalized cells such as nerve cells, glial cells or peripheral blood mononuclear cells may be used to prepare suitable host cells for HMSV, and such cells can be transformed with HMSV particles, or nucleic acid.

Yet another application of the invention is its use in a method for producing antibodies, preferably neutralizing antibodies, to HMSV comprising administering to an individual an isolated immunogenic polypeptide containing an HMSV epitope in an amount sufficient to produce a humoral and/or cellular immune response.

SEQ ID NOS: 1, 2, 3, 4, 5 and 6 illustrate cDNA sequences of importance in the invention. These sequences may be produced by synthetic means known per se.

Definitions

The term "HMSV", as used herein, denotes a viral species which causes or is associated with MS, and attenuated strains or defective interfering particles derived therefrom. The HMSV genome is comprised of RNA. It is known that RNA containing viruses have relatively high rates of spontaneous mutation, i.e., reportedly on the order of $10^{-3}$ to $10^{-4}$ per nucleotide. Therefore, there are multiple strains within the HMSV species described infra. The compositions and methods described herein enable the identification, detection, and isolation of the various related strains. Moreover, they also allow the preparation of diagnostics and vaccines for the various strains, and have utility in screening procedures for anti-viral agents for pharmacologic use in that they inhibit replication of HMSV.

The information provided herein, although derived from one strain of HMSV, hereinafter referred to as HMSV-1, is sufficient to allow a viral taxonomist to identify other strains which fall within the species. As described herein, we have discovered that HMSV is a retrovirus or a retroviral-like virus. The morphology and composition of retroviruses are known.

HMSV encodes an epitope which is immunologically identifiable with an epitope in the HMSV genome from which the sequences described herein are derived; preferably the epitope is encoded in a cDNA described herein. Methods for determining immunological reactivity are known in the art, for example, by radioimmunoassay, by ELISA assay, by haemagglutination.

In addition to the above, the following parameters are applicable, either alone or in combination, in identifying a strain as HMSV. Since HMSV strains are evolutionarily related, it is expected that the overall homology of the genomes at the nucleotide level will be 60% or greater, preferably 65, 70 or 75% or greater, and even more preferably 80, 85, 90 or 95% or greater; and in addition that there will be corresponding contiguous sequences of at least about 13 nucleotides. The correspondence between a putative HMSV strain genomic sequence and the HMSV-1 cDNA sequence can be determined by techniques known in the art.

Because of the evolutionary relationship of the strains of HMSV, putative HMSV strains are identifiable by their homology at the polypentide level. Generally, HMSV strains are more than 40% homologous, preferably more than 60, 65, 70 or 75% homologous, and even more preferably more than 80, 85 or 90% homologous at the polypeptide level. The techniques for determining amino acid sequence homology are known in the art. For example, the amino acid sequence may be determined directly and compared to the sequences provided herein. For example also, the nucleotide sequence of the genomic material of the putative HMSV may be determined (usually via a cDNA intermediate); the amino acid sequence encoded therein can be determined, and the corresponding regions compared.

As used herein, a polynucleotide "derived from" a designated sequence, for example, the HMSV cDNA, particularly one of those exemplified in the sequences of SEQ ID NOS: 1, 2, 3, 4, 5 or 6, or from an HMSV genome, refers to a polynucleotide sequence which is comprised of a sequence of at least 6 nucleotides, is preferably at least 8 nucleotides, is more preferably at least 10–12 nucleotides, and even more preferably at least 15–25 nucleotides corresponding, i.e., homologous, to a region of the designated nucleotide sequence. Preferably, the sequence of the region from which the polynucleotide is derived is homologous to a sequence which is unique to an HMSV genome. Complementary sequences of such homologues also form part of the present invention. Whether or not a sequence is unique to the HMSV genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are retroviral agents, e.g., HIV-1 or HIV-2. The correspondence or non-correspondence of the derived sequence to other sequences can also be determined by hybridization under the appropriate stringency conditions. Hybridization techniques for determining the complementarity of nucleic acid sequences are known in the art.

The derived polynucleotide is not necessarily physically derived from the nucleotide sequence shown, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

Homologous polynucleotides include those in which genetic code within an open reading frame has been altered to provide for substantially the same amino acid sequence but with changed codon usage. Alteration of codon usage can be introduced for example to increase the efficiency of expression in recombinant host cell systems.

Similarly, a polypeptide or amino acid sequence derived from a designated nucleic acid sequence, for example, one of the sequences in SEQ ID NOS: 1, 2, 3, 4, 5 or 6 or from an HMSV genome, refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence.

Polypeptides which are immunologically identifiable with HMSV polypeptides may also be mimeotopes, ie polypeptides of unrelated sequence but with a 3-dimensional structure corresponding to an HMSV epitope, ie. the mimeotope is capable of being bound by an antibody to HMSV.

A recombinant or derived polypeptide is not necessarily translated from a designated nucleic acid sequence, for example, one of the sequences in SEQ ID NOS: 1, 2, 3, 4, 5 or 6 or from an HMSV genome; it may be generated in any manner, including for example, chemical synthesis, or expression of a recombinant expression system, or isolation from mutated HMSV.

The term "recombinant polynucleotide" as used herein intends a polynucleotide of genomic, cDNA, semisynthetic, or synthetic origin which, by virtue of its origin or manipulation: (1) is not associated with all or a portion of the polynucleotide with which it is associated in nature or in the form of a library; and/or (2) is linked to a polynucleotide other than that to which it is linked in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single stranded RNA. It also includes modified, for example, by methylation and/or by capping, and unmodified forms of the polynucleotide.

As used herein, the term "HMSV containing a sequence corresponding to a cDNA" means that the HMSV contains a polynucleotide sequence which is homologous to or complementary to a sequence in the designated DNA; the degree of homology or complementarity to the cDNA will be as described above.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A "replicon" is any genetic element, e.g., a plasmid, a chromosome, a virus, that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Immunologically identifiable with/as" refers to the presence of epitope(s) and polypeptides(s) which are also present in and are unique to the designated polypeptide(s), usually HMSV proteins. Immunological identity may be determined by antibody binding and/or competition in binding; these techniques are known to those of average skill in the art.

The uniqueness of an epitope can also be determined by computer searches of known data banks, e.g. Genebank, for the polynucleotide sequences which encode the epitope, and by amino acid sequence comparisons with other known proteins.

As used herein, "epitope" refers to an antigenic determinant of a polypeptide; an epitope could comprise 3 amino acids which are contiguous or brought together by the secondary or tertiary structure of the polypeptide in a spatial conformation which is unique to the epitope, generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

Antibodies may be monoclonal or polyclonal. For the purposes of this invention, the term "antibody", unless specified to the contrary, includes fragments of whole antibodies which retain their binding activity for a tumour target antigen. Such fragments include Fv, F(ab') and $F(ab')_2$ fragments, as well as single chain antibodies. Furthermore, the antibodies and fragments thereof may be humanised antibodies, eg. as described in EP-A-239400.

Antibodies according to the invention may be produced by conventional hybridoma techniques or, in the case of modified antibodies or fragments, by recombinant DNA technology, eg by the expression in a suitable host vector of a DNA construct encoding the modified antibody or fragment operably linked to a promoter. Suitable host cells include bacterial (eg. *E.coli*), yeast, insect and mammalian.

As used herein, the term "immunogenic polypeptide containing an HMSV epitope" includes naturally occurring HMSV polypeptides or fragments thereof, as well as polypeptides prepared by other means, for example, chemical synthesis, or the expression of the polypeptide in a recombinant organism.

The term "polypeptide" refers to a molecular chain of amino acids and does not refer to a specific length of the product; thus, peptides, oligopeptides, and proteins are included within the definition of polypeptide. This term also does not refer to post-expression modifications of the polypeptide, for example, glycosylations, acetylations, phosphorylations and the like. The term does not refer to the source of the polypeptide which may be obtained by any suitable means, eg, recombinantly or synthetically.

"Transformation", as used herein, refers to the insertion of an exogenous polynucleotide into a host cell, irrespective of the method used for the insertion, for example, direct uptake, transduction, or f-mating. The exogenous polynucleotide may be maintained as a non-integrated vector, for example, a plasmid, or alternatively, may be integrated into the host genome.

"Treatment" as used herein refers to prophylaxis and/or therapy.

As used herein, the "plus strand" of a nucleic acid contains the sequence that encodes the polypeptide. The "minus strand" contains a sequence which is complementary to that of the "plus strand".

As used herein, a "positive stranded genome" of a virus is one in which the genome is single-stranded and which encodes a viral polypeptide(s). Examples of positive stranded RNA viruses include Togaviridae, Coronaviridae, Retroviridae, Picbrnaviridae, and Caliciviridae.

As used herein, "antibody containing body component" refers to a component of an individual's body which is a source of the antibodies of interest. Antibody containing body components are known in the art, and include but are not limited to, for example, plasma, serum, spinal fluid, lymph fluid, the external secretions of the respiratory, intestinal, and genitourinary tracts, tears, saliva, milk, white blood cells, and myelomas.

As used herein, "purified HMSV" refers to a preparation of HMSV which has been isolated from the cellular constituents with which the virus is normally associated, and from other types of viruses which may be present in the infected tissue. The techniques for isolating viruses are known to those of skill in the art, and include, for example, centrifugation and affinity chromatography.

The practice of the present invention will employ, unless otherwise indicated, conventional techniques of molecular biology, microbiology, recombinant DNA, and immunology, which are within the skill of the art. Such techniques are explained fully in the literature. See e.g., Maniatis, Fitsch & Sambrook, MOLECULAR CLONING; A LABORATORY MANUAL (1982); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker. eds. (1927), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, New York), and HANDBOOK OF EXPERIMENTAL IMMUNOLOGY, VOLUMES I–IV (D. M. Weir and C. C. Blackwell eds 1986).

The useful materials and processes of the present invention are made possible by the provision of nucleotide sequences derived from sequences present in MS patients sera.

The availability of the sequence information shown in SEQ ID NOS: 1, 2, 3, 4, 5 and 6 permits the construction of DNA probes and polypeptides useful in diagnosing HMSV due to HMSV infection. For example, from these sequences it is possible to synthesize DNA oligomers of about 8–10 nucleotides, or larger, eg. 15, 18, 20 or 25 or more nucleotides one or more of which are useful as hybridization probes to detect the presence of the viral genome. These sequences also allow the design and production of HMSV specific polypeptides which are useful as diagnostic reagents for the presence of antibodies raised by an individual exposed to MS. Antibodies to purified polypeptides derived from the sequence information may also be used to detect viral antigens in infected individuals and in other body fluids and tissue such as blood.

Knowledge of these sequences also enable the design and production of polypeptides which may be used as vaccines against HMSV and also for the production of antibodies, which in turn may be used for protection against the disease, and/or for therapy of HMSV infected individuals.

Because we have identified a retrovirus as being the causative agent of MS or at least as being associated with the disease MS, this opens up the possibility of treatment of MS patients with pharmaceutical agents which are effective in the treatment or prophylaxis of human immunodeficiency virus (HIV). Accordingly, the invention provides:

(i) the use of a pharmaceutical agent which is effective in the treatment or prophylaxis of HIV for the manufacture of a medicament for the treatment or prophylaxis of MS; and (ii) a method of treating MS or ameliorating the symptoms thereof which comprises administering to an individual with MS an effective amount of a pharmaceutical agent which is effective in the treatment or prophylaxis of HIV.

Examples of suitable pharmaceutical agents include AZT and ddI.

EXAMPLES

Example 1

Using probes derived from the sequences of SEQ ID NOS: 1–6 derived from Example 1, further nucleic acid samples from MS individuals are probed, to confirm the presence of HMSV nucleic acid. Libraries from such individuals are constructed, starting with either total nucleic acid or total RNA. Probes derived from SEQ ID NOS: 1–6 are used to identify members of the library which contain HMSV sequences. Positive clones are sequenced, and the 3' or 5' regions of the clones are used as probes to identify further HMSV positive clones. Using this genome walking technique, the total HMSV genomic sequence is derived.

What is claimed is:

1. An isolated polynucleotide comprising a sequence of nucleotides having at least 60% homology to a nucleotide sequence selected from the group consisting of SEQ ID NOS:1 to 6 and fully complementary sequences to SEQ ID NOS:1 to 6, and which said sequence of nucleotides is capable of selectively hybridizing to the single positive stranded genome of the human multiple sclerosis virus (HMSV) or to the negative stranded complement thereof, wherein HMSV is characterized by:

(i) a positive stranded RNA genome;

(ii) said genome encoding a reverse transcriptase enzyme; and (iii) said genome comprising nucleotide sequences which comprise one of the nucleotide sequences illustrated in SEQ ID NOS:1–6.

2. An isolated polynucleotide according to claim 1 which comprises any one of SEQ ID NOS: 1, 2, 3, 4, 5 or 6.

3. Isolated polynucleotide probe comprising a polynucleotide according to claim 1 linked to a detectable label.

4. A recombinant vector comprising an isolated polynucleotide according to claim 1.

5. An expression vector comprising an isolated polynucleotide according to claim 1 operably linked to a control sequence compatible with a desired host cell.

6. A host cell transformed with a vector according to claim 4.

7. The isolated polynucleotide according to claim 1, wherein at least about 13 contiguous nucleotides in said sequence are identical with the nucleotide sequence selected from the group consisting of SEQ ID NOS:1 to 6 and fully complementary sequences to SEQ ID NOS:1 to 6.

8. The isolated polynucleotide according to claim 1, wherein said sequence of nucleotides has at least 85% homology to a nucleotide sequence selected from the group consisting of SEQ ID NOS:1 to 6 and fully complementary sequences to SEQ ID NOS:1 to 6.

9. The isolated polynucleotide according to claim 1, wherein said sequence of nucleotides has at least 90% homology to a nucleotide sequence selected from the group consisting of SEQ ID NOS:1 to 6 and fully complementary sequences to SEQ ID NOS:1 to 6.

10. The isolated polynucleotide according to claim 1, wherein said sequence of nucleotides has at least 95% homology to a nucleotide sequence selected from the group consisting of SEQ ID NOS:1 to 6 and fully complementary sequences to SEQ ID NOS:1 to 6.

11. The isolated polynucleotide according to claim 1, which encodes a polypeptide, wherein said nucleotide sequence has at least 13 contiguous nucleotides identical with a nucleotide sequence selected from the group consisting of SEQ ID NOS:1 to 6 and fully complementary sequences to SEQ ID NOS:1 to 6.

12. The isolated polynucleotide according to claim 1, which encodes a polypeptide, wherein said nucleotide sequence is at least 85% homologous to a nucleotide sequence selected from the group consisting of SEQ ID NOS:1 to 6 and fully complementary sequences to SEQ ID NOS:1 to 6.

13. The isolated polynucleotide according to claim 1, which encodes a polypeptide, wherein said nucleotide sequence is at least 90% homologous to a nucleotide sequence selected from the group consisting of SEQ ID NOS:1 to 6 and fully complementary sequences to SEQ ID NOS:1 to 6.

14. The isolated polynucleotide according to claim 1, which encodes a polypeptide, wherein said nucleotide sequence is at least 95% homologous to a nucleotide sequence selected from the group consisting of SEQ ID NOS:1 to 6 and fully complementary sequences to SEQ ID NOS:1 to 6.

15. A method for detecting the presence of a nucleic acid from HMSV in a sample, which comprises:
  (a) contacting the sample with a polynucleotide probe comprising a polynucleotide of claim 1 under conditions which allow the formation of a polynucleotide duplex between said probe and the nucleic acid of HMSV; and
  (b) detecting said duplex, wherein HMSV is characterized by:
    (i) a positive stranded RNA genome;
    (ii) said genome encoding a reverse transcriptase enzyme; and
    (iii) said genome comprising nucleotide sequences which comprise one of the nucleotide sequences illustrated in SEQ ID NOS:1–6 or which comprise a nucleotide sequence having at least 60% homology to one of the nucleotide sequences of SEQ ID NOS:1–6.

16. A method according to claim 15, further comprising the steps of a polymerase chain reaction (PCR).

17. An isolated polypeptide encoded by a polynucleotide selected from the group consisting of SEQ ID NO:1, SEQ ID NO:2, SEQ ID NO:3, SEQ ID NO:4, SEQ ID NO:5, SEQ ID NO:6, wherein said isolated polypeptide comprises an antigenic determinant of HMSV.

18. Isolated polypeptide according to claim 17 attached to a solid substrate.

19. Isolated polypeptide according to claim 17 attached to a detectable label.

20. An isolated peptide fragment of the polypeptide of claim 17, wherein said peptide fragment comprises a sequence of at least 10 amino acids.

\* \* \* \* \*